United States Patent [19]

Piunti

[11] Patent Number: 5,800,476

[45] Date of Patent: *Sep. 1, 1998

[54] METHOD FOR IMPROVING CERTAIN FUNCTIONAL CHARACTERISTICS OF THE HUMAN BODY

[75] Inventor: Luigi Piunti, Porto D'Ascoli, Italy

[73] Assignee: Galaxy Top International S.p.A., Ascoli Piceno, Italy

[*] Notice: This patent issued on a continued prosecution application filed under 37 CFR 1.53(d), and is subject to the twenty year patent term provisions of 35 U.S.C. 154(a)(2).

[21] Appl. No.: 733,960

[22] Filed: Oct. 21, 1996

[51] Int. Cl.$^6$ .................................................. A61N 1/36
[52] U.S. Cl. .................................................. 607/66
[58] Field of Search ........................... 607/74, 46, 48, 607/40, 66, 68, 70

[56] References Cited

U.S. PATENT DOCUMENTS

| | | | |
|---|---|---|---|
| 4,121,594 | 10/1978 | Miller et al. | 607/74 |
| 4,919,139 | 4/1990 | Brodard | 607/74 |
| 5,097,833 | 3/1992 | Campos | 607/68 |
| 5,188,104 | 2/1993 | Wernicke et al. | 607/40 |
| 5,342,410 | 8/1994 | Braverman | 607/46 |
| 5,458,625 | 10/1995 | Kendall | 607/58 |

Primary Examiner—William E. Kamm
Assistant Examiner—George R. Evanisko
Attorney, Agent, or Firm—McAulay Fisher Nissen Goldberg & Kiel, LLP

[57] ABSTRACT

According to a method for improving certain functional characteristics of the human body, a wave is generated with a shape that is asymmetric with respect to a basic line, and with predetermined frequency and amplitude. A number of waves are grouped into pulse trains (1), with predetermined time gaps between one train and the following one. The pulse trains are in turn grouped into timely separated predetermined sequences that are applied to the human body or to a part thereof. The pulse train sequences provoke in the body a sequence of stimuli that lead to improvement of certain functional characteristics of the body.

6 Claims, 8 Drawing Sheets

IMPROVEMENT OF CARTILAGINOUS PARTS ELASTICITY

| STEPS | | TYPE OF STIMULUS | WAVE FREQUENCY | WAVE TRAIN FORM | WAVE TRAINS FREQUENCY | NOTES |
|---|---|---|---|---|---|---|
| P1 | 1) 15' | CONTINUOUS WITH LOW FREQUENCY | 8 Hz | NONE (CONTINUOUS GENERATION) | NONE (CONTINUOUS GENERATION) | // |
| P2 | 2) 15' | CONTINUOUS WITH LOW FREQUENCY | 2 Hz | NONE (CONTINUOUS GENERATION) | NONE (CONTINUOUS GENERATION) | // |
| | 3) | // | // | // | // | // |
| | 4) | // | // | // | // | // |

FIG. 8

METHOD FOR IMPROVING CERTAIN FUNCTIONAL CHARACTERISTICS OF THE HUMAN BODY

BACKGROUND OF THE INVENTION

The invention relates to a method for improving certain functional characteristics of the human body, in particular the ones concerning muscles tone and blood circulatory system.

DESCRIPTION OF THE PRIOR ART

As it is known, nowadays, people lead quite a sedentary life, often in conjunction with very little physical activity and much intellectual work.

In other words, today's man is too often subjected to psycho-social stimuli which involve mainly activation of emotions almost never followed by a proper physical vent, that could relieve the whole organism of an emotional charge accumulated during a person's social life.

The problem of balancing the human body functional characteristics, with particular reference to those psycho-physical, was known even in the most ancient times.

Not by chance we know the saying of the ancient Romans—"mens sana in corpore sano"—according to which a person's intellectual activity is preserved when his physical health is kept in best conditions.

Therefore, there is an actual necessity to keep a man as physically active as possible in order to preserve those of his functional characteristics, such as muscles tone and blood circulation, that deteriorate mainly due to little physical activity.

Hence, a person can practice predetermined physical activities or subject himself to passive methodologies carried out by techniques, apparatuses and medical substances which have been known for a long time.

Leaving out the medical substances and biomedical or physiotherapeutic apparatuses, in that they are beyond the present invention, the methods used for this purpose can be divided in "manual", "mechanical" and "electronic".

From the first group we can mention the traditional method of "manual" massage, performed by an experienced operator, usually physiotherapist, on a body or a part of a body of a person to be massaged.

The "mechanical" methods are substantially based on an automatic massage performed on the body or parts of the body of the person to be treated, by suitable apparatuses.

The hydromassage is a methodology that is included in this class, because it exploits the action of a jet of water mixed with air microbubbles in order to perform a massage.

The "electronic" methods are based on irradiation of the body or parts of the body of a person by known electromagnetic radiation of determined frequency, like e.g. infrared radiation.

According to another procedure, the body of the person is exposed to localized or diffused heat, as e.g. in sauna technique.

Almost all these techniques must be performed on a person for a relatively long period of time and, moreover, an operator experienced in applying these techniques must be present.

SUMMARY OF THE INVENTION

The main object of the present invention is to propose a method for improving certain functional characteristics of the human body, that can be employed in reasonably short time and without help of specialized operators.

Another object of the present invention is to propose a method that can be applied to the human body in a simple way, and that is extremely efficient in improving its functional characteristics.

The above mentioned objects are obtained in accordance with the invention by means of a method for improving particular functional characteristics of the human body, that includes generation of waves in a form made up of a positive peak and a negative peak, situated over and under a basic line, respectively.

These waves are generated with predetermined frequency and amplitude and with predetermined intervals of time between one another, so as to define pre-established wave trains that are grouped in timely separated prefixed sequences and pass through human body or its part.

The so obtained sequences provoke a predetermined series of stimuli which improve particular functional characteristics.

BRIEF DESCRIPTION OF DRAWINGS

The characteristics of the invention will be better understood from the following description, with particular reference to the attached drawings, in which.

DISCLOSURE OF THE INVENTION

Figure 1:
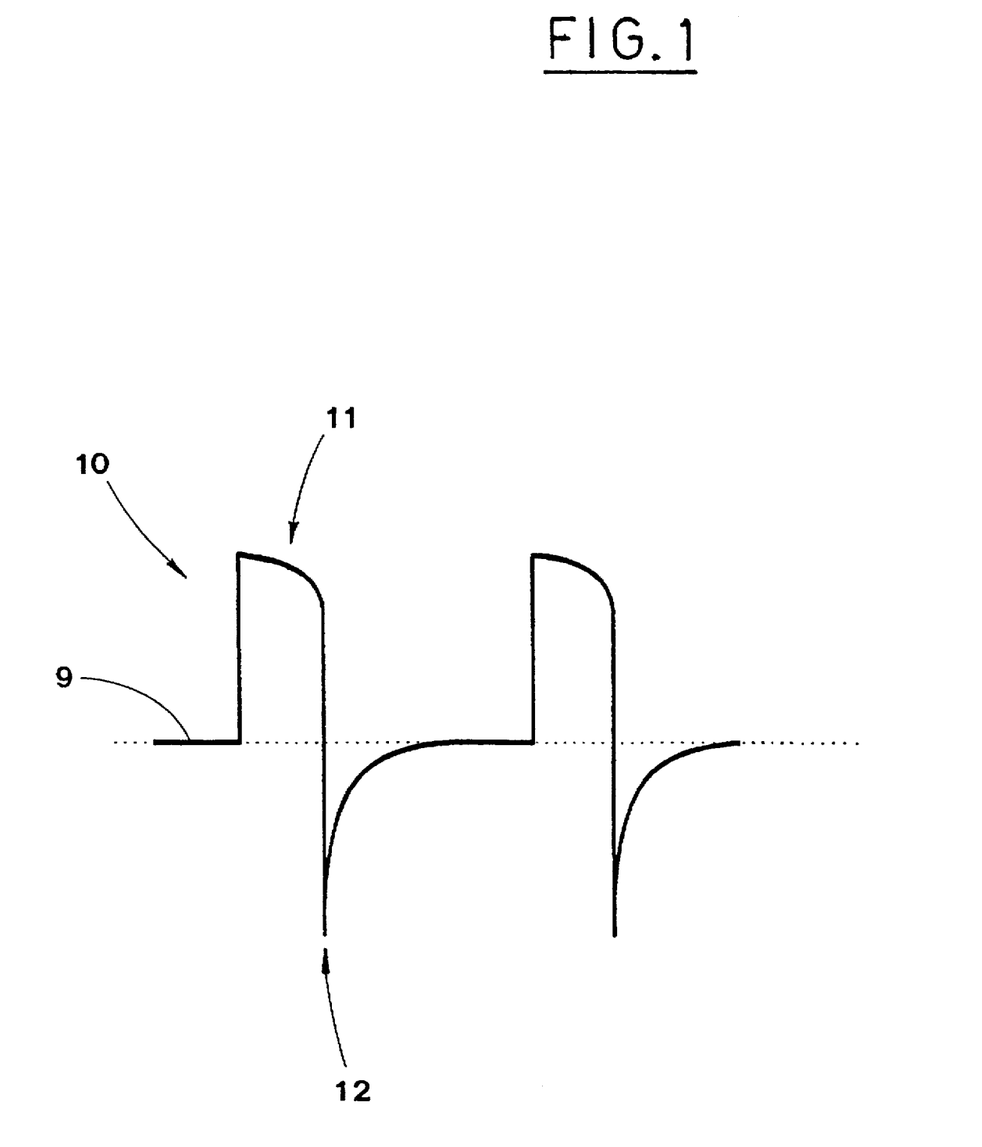
FIG. 1 shows a couple of wave forms used in accordance with the method being the subject of the present invention.

With reference to FIG. 1, number 10 indicates a wave form, asymmetrical with respect to a basic line 9 and including a positive peak 11 and a negative peak 12, respectively over and under the basic line 9.

The maximum amplitude of both the positive peak 10 and the negative peak 12 of the wave form 10 is not bigger than e.g. 80 volt, while the duration of the positive peak is preferably of 0,12 ms (millisecond).

According to the method, pre-established wave trains 1 are generated, constituted by the waves 10 that have predetermined frequencies and amplitudes and are separated with such time intervals as to define prefixed stimuli.

Moreover, according to the method, prefixed wave trains 1, suitably timely separated, are arranged in a pre-established sequence S.

The so arranged waves are applied to the human body or its part to provoke a desired sequence of stimuli that cause improvement of particular functional characteristics.

Furthermore, according to the method, the so generated sequences S of wave trains 1 are supplied in predetermined steps so as to improve specific functional characteristics of the human body subjected to the action of these sequences S of wave trains 1.

Figure 2:
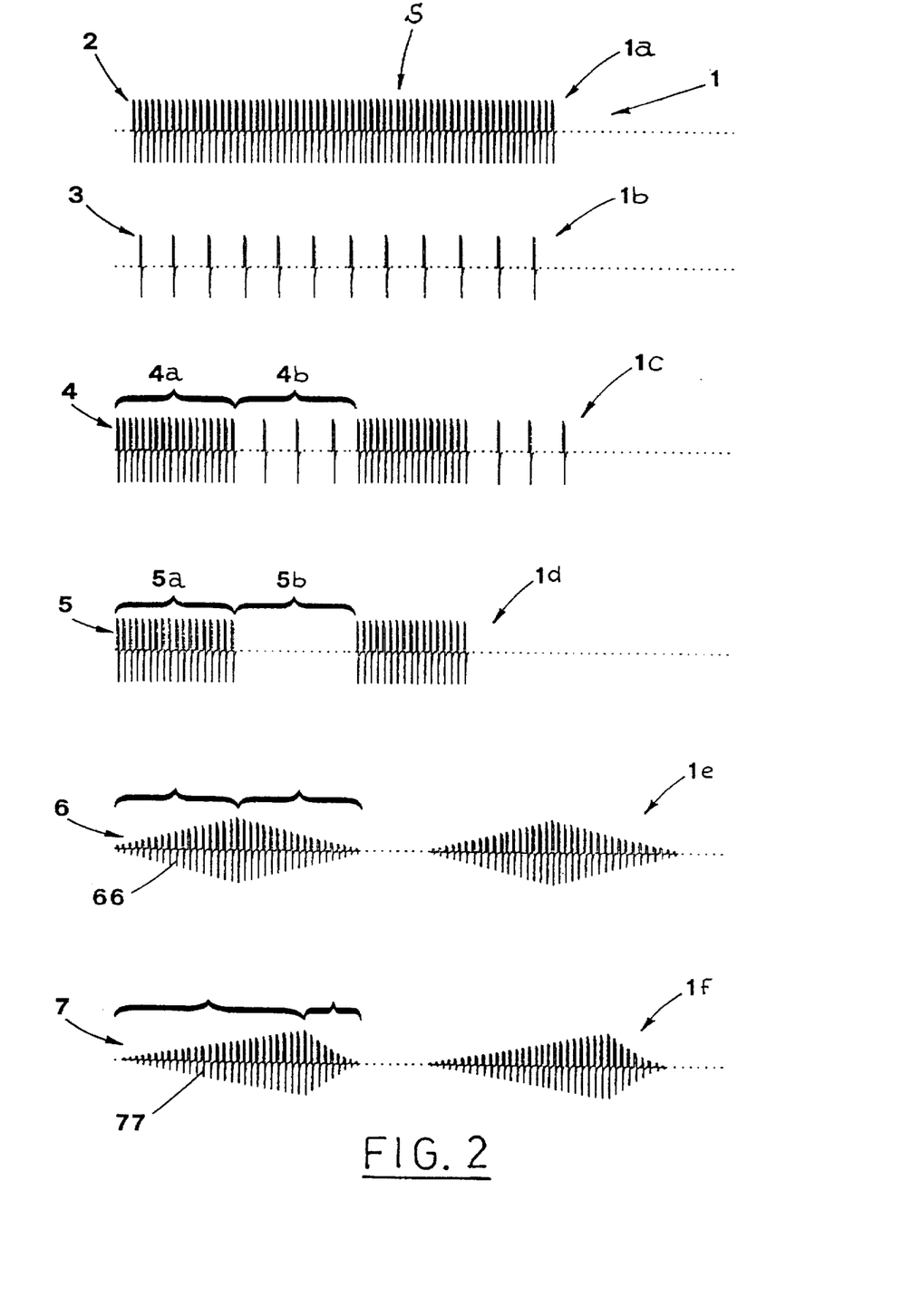
FIG. 2 shows the sequences of wave trains used in accordance with the method being the subject of the present invention.

With reference to FIG. 2, the wave trains 1 used for formation of the predetermined sequences S will be described in a detailed way.

It will be understood that the frequency of the wave 10 used in these wave trains 1 varies preferably from 2 to 100 hertz.

A first wave train 1a includes waves 10 of 100 hertz frequency and the sequence S of these first wave trains 1a generates in the human body a continuous stimulus 2 of high frequency.

A second wave train 1b includes waves 10 of 2 hertz frequency and the sequence S of these second wave trains 1b generates in the human body a continuous stimulus 3 of low frequency.

A third wave train 1c includes a first bunch 4a of waves 10 of 100 hertz frequency followed by a second bunch 4b of waves 10 of 2 hertz frequency.

The period of the first bunch 4a and of the second bunch 4b is the same and the sequence S of a group of these third wave trains 1a generates in the human body a continuous stimulus 4 of alternated frequency.

A fourth wave train 1d is constituted by a bunch 5a of waves 10 of 100 hertz frequency followed by a time interval 5b without any wave 10 and as long as the said bunch 5a.

The sequence S of so formed wave trains 1d generates in the human body an intermittent stimulus S.

A fifth wave train 1e includes waves 10 of 100 hertz frequency.

At the extremities of this fifth train 1e the amplitude of the waves decreases nearly to zero, while in the middle of the train 1e the amplitude reaches its maximum value (about 80 volt for both the positive peak 11 and the negative peak 12), so that the same train has the shape of a rhombus 66.

The sequence S of these wave trains 1e generates in the human body a symmetrical stimulus 6 of variable amplitude.

A sixth wave train 1f includes waves 10 of 100 hertz frequency.

At the extremities of this sixth train 1f the amplitude of the waves decreases nearly to zero, while at about two thirds of the length of the train 1f the amplitude reaches its maximum value (about 80 volt for both peaks), so that the same train has the shape of an arrow 77.

The sequence S of these sixth wave trains 1f generates in the human body an asymmetrical stimulus 7 of variable amplitude.

Now, a detailed description of the method steps will follow, concerning respectively each of particular functional characteristics of the human body subjected to a combination of predetermined sequences S of the above mentioned wave trains 1.

Figure 3:
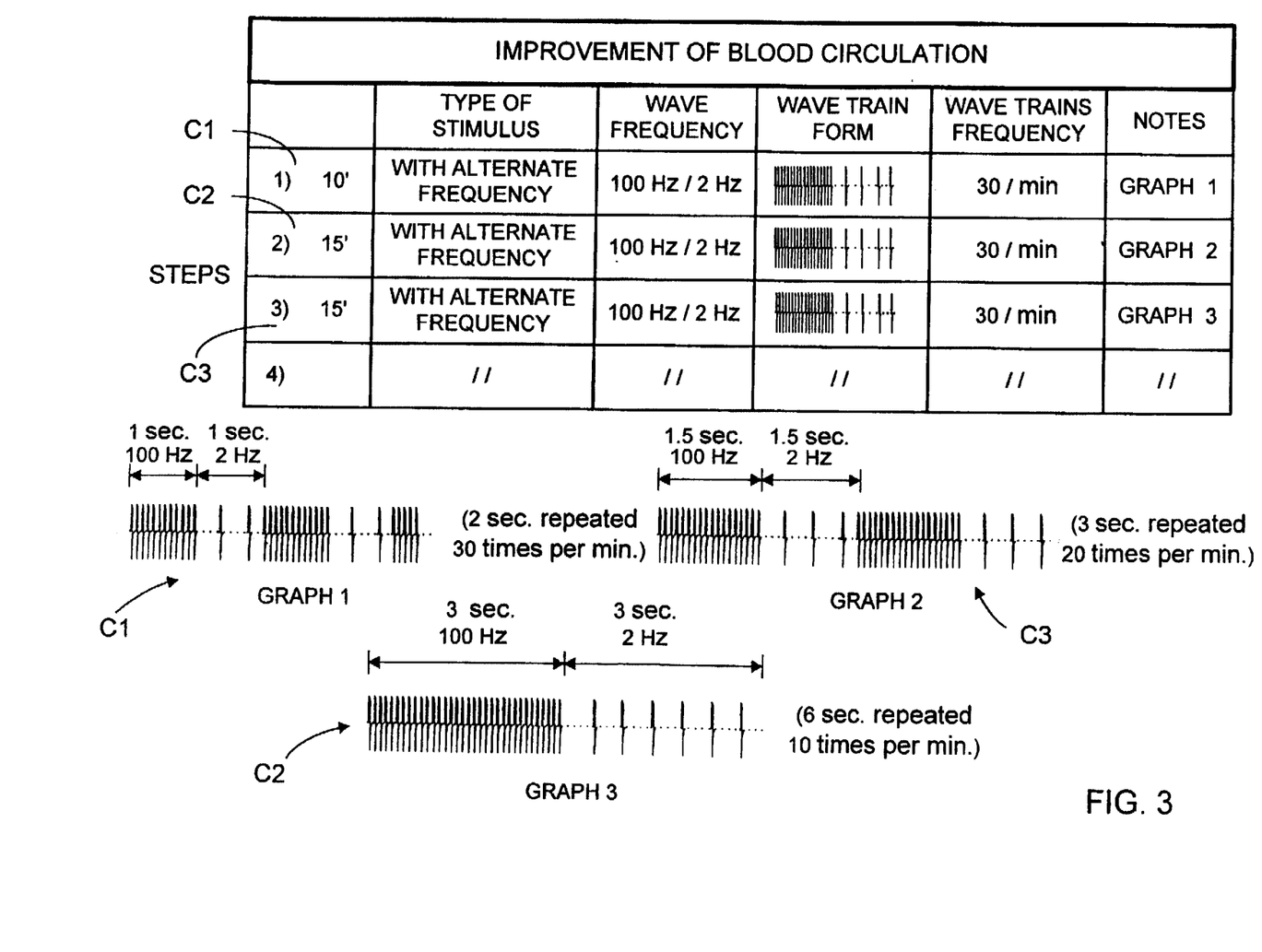
FIGS. 3 to 8 show different steps of the method for improving some functional characteristics of the human body.

With reference to FIG. 3, a sequence formed by a first step C1, a second step C2 and third C3, each one described in the following, is applied to the human body and is designed to improve blood circulation.

The first step C1 lasts 10 minutes and employs the third wave train 1c in which each bunch, first 4a and second 4b, lasts 1 sec.

The second step lasts 15 minutes and employs again the third wave train 1c in which each bunch, first 4a and second 4b, lasts 1.50 sec.

The third step C3 lasts 15 minutes and employs the third wave train 1c in which each bunch, first 4a and second 4b, lasts 3 sec.

Figure 4:
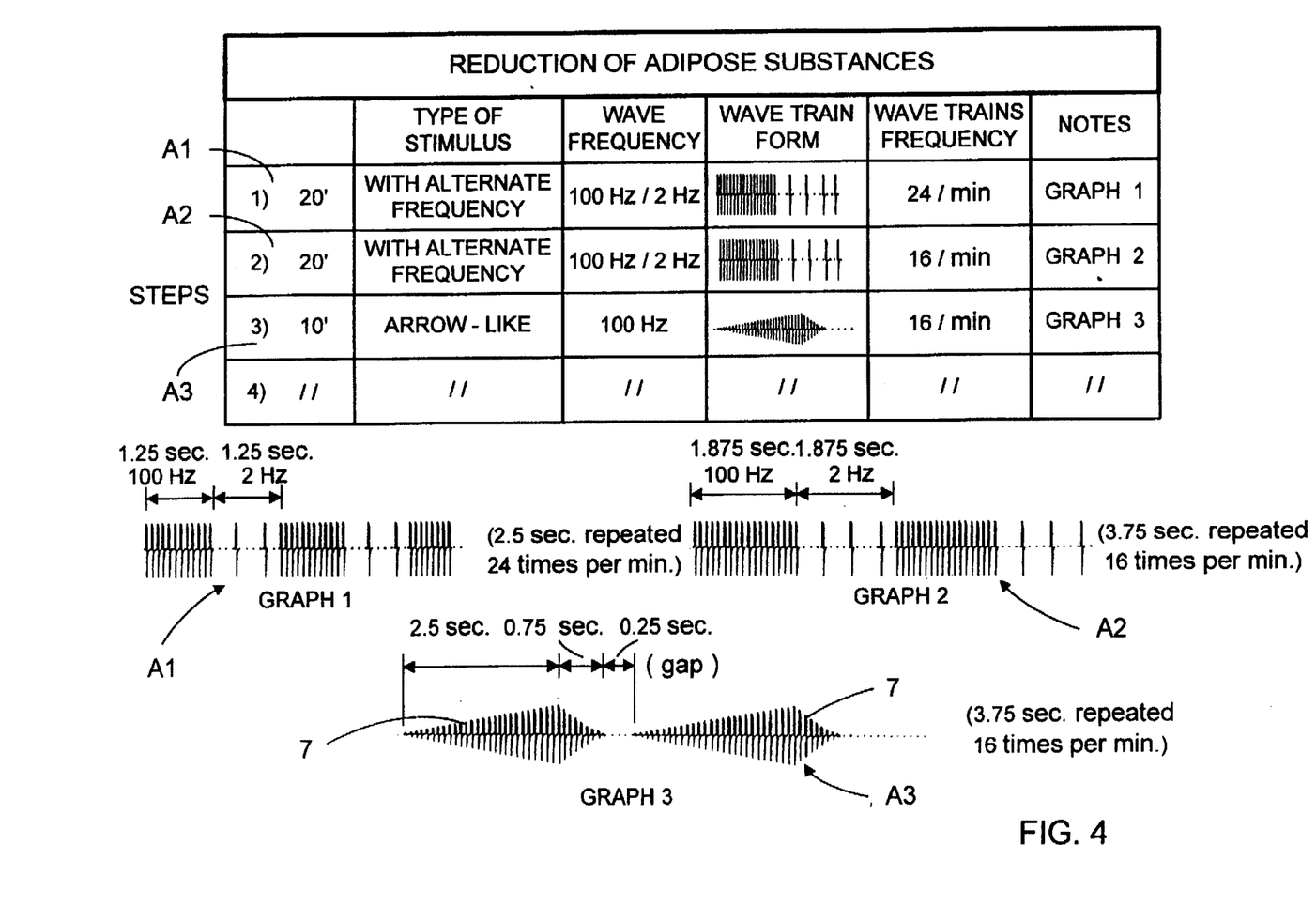

According to FIG. 4, which shows a second application of the method, a sequence S of wave trains 1 applied to the human body or its part, includes a first step, a second step, and a third step A1, A2, A3 and respectively.

The first step A1 lasts 20 minutes and employs the third wave train 1c, whose bunches, first 4a and second 4b, last 1.25 sec.

The first step A1 is followed by a second step A2, which lasts 20 minutes and employs the third wave trains 1c, whose bunches, first 4a and second 4b, last 1.875 sec.

Then a third step A3 follows, which lasts 10 minutes and employs the sixth wave trains 1f in the form of an arrow 77, each of the wave trains being made up of waves 10, whose amplitude is increasing for a period of 2.75 sec., and of waves 10, whose amplitude is decreasing for a period of 0.75 sec.

These sixth wave trains, shaped like arrow 77, are timely separated with intervals of 0.25 sec. one from another.

The sequence of the steps A1, A2 and A3 improves the reduction of adipose substances present in the human body subjected to this technique.

Figure 5:
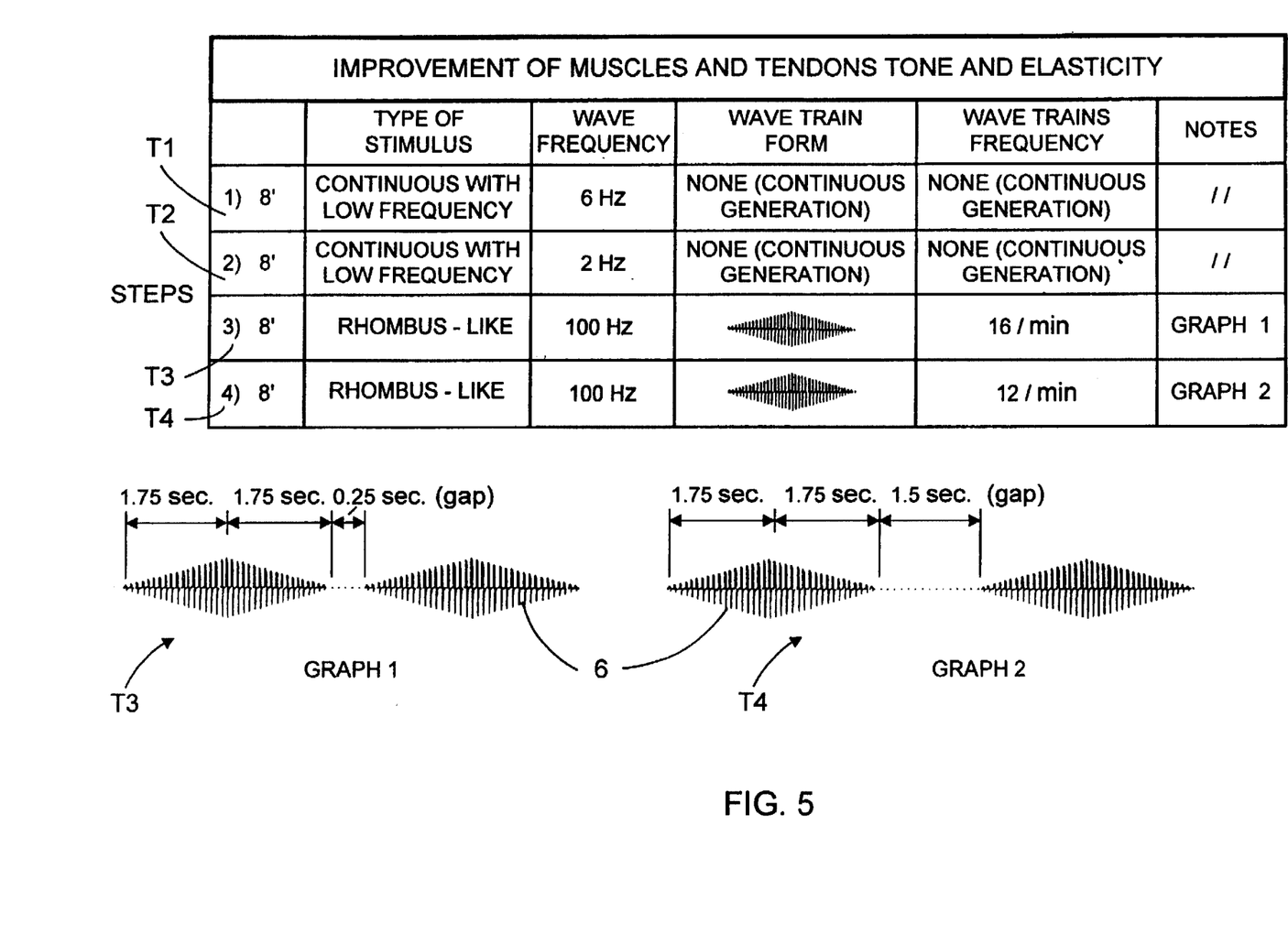

According to a third application of the method, illustrated in FIG. 5, the sequence S applied to the human body or its part is performed as a series of predetermined steps, first T1, second T2, third T3 and fourth T4, which increase and improve muscles tone and elasticity in the human body.

The first step T1 lasts 8 minutes and employs continuously waves 10 of 6 hertz frequency, while the second step T2, lasting 8 minutes, employs continuously waves 10 of 2 hertz frequency.

These two steps are followed by the third step T3, which lasts 8 minutes and employs the fifth wave train 1e.

The trains 1e have the shape of the rhombus 66 and last 3.50 sec. with a 0.25 sec. gap between one another.

The only difference between the fourth step T4 and the third step T3 is the length of the train gaps, which in the fourth step T4 is 1.50 sec.

Figure 6:
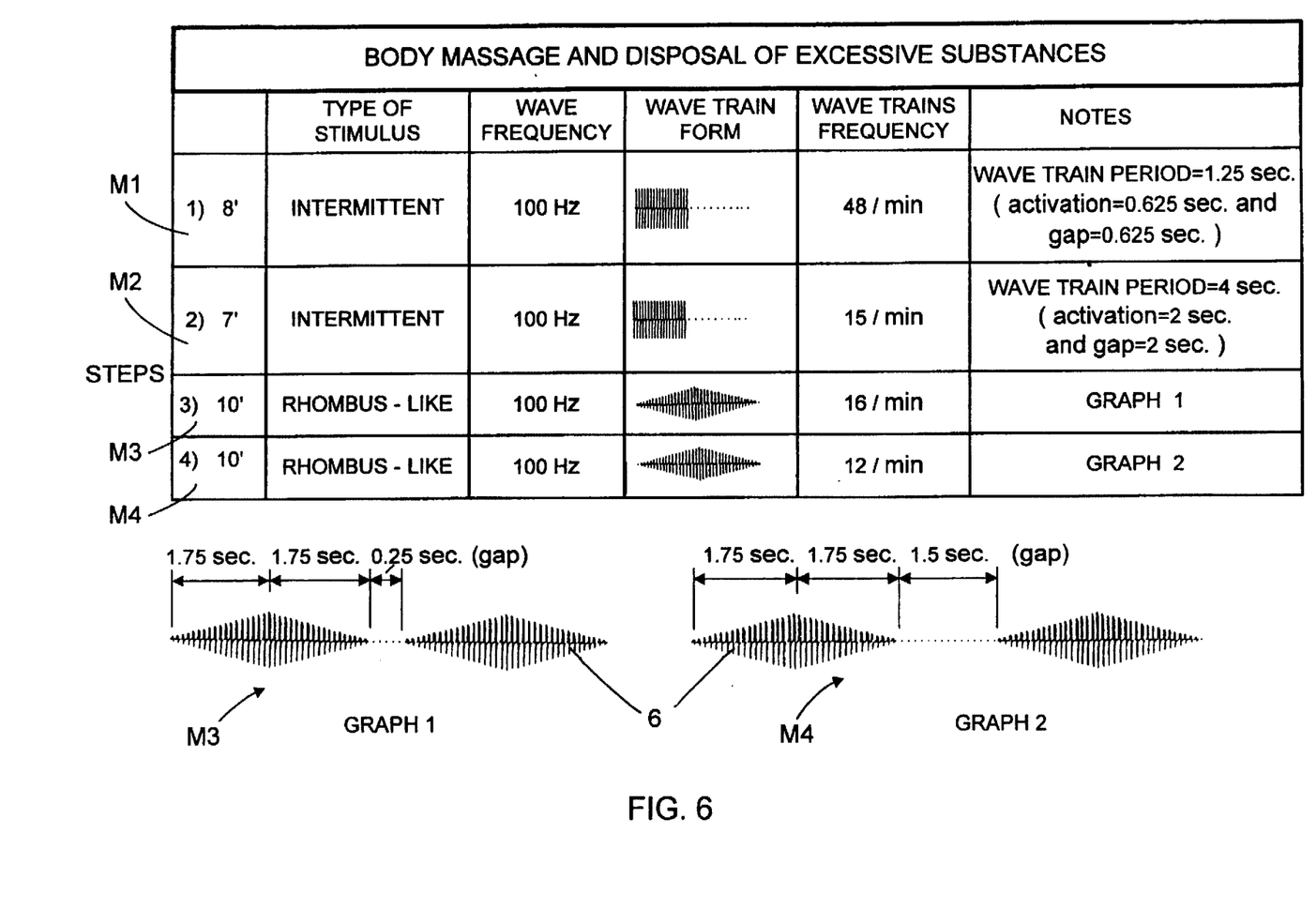

FIG. 6 illustrates a fourth application of the method, that includes a sequence of four predetermined steps first M1, second M2, third M3 and fourth M4.

These steps determine the massage of the human body to improve disposal of excessive substances thereof and regulates its weight.

The first step M1, lasting 8 minutes, employs the fourth wave train 1d of 1.25 sec. period, while the second step M2 differs from the first one, because it lasts 7 minutes and the fourth wave train 1d period is of 4 sec.

These two steps are followed by the third step M3, that lasts 10 minutes and includes fifth wave trains 1e, each one having a period of 3.50 sec. and timely separated from the previous one by intervals of 0.25 sec.

The following fourth step M4 lasts 10 minutes and has 1.50 sec. intervals between the fifth wave trains.

Figure 7:
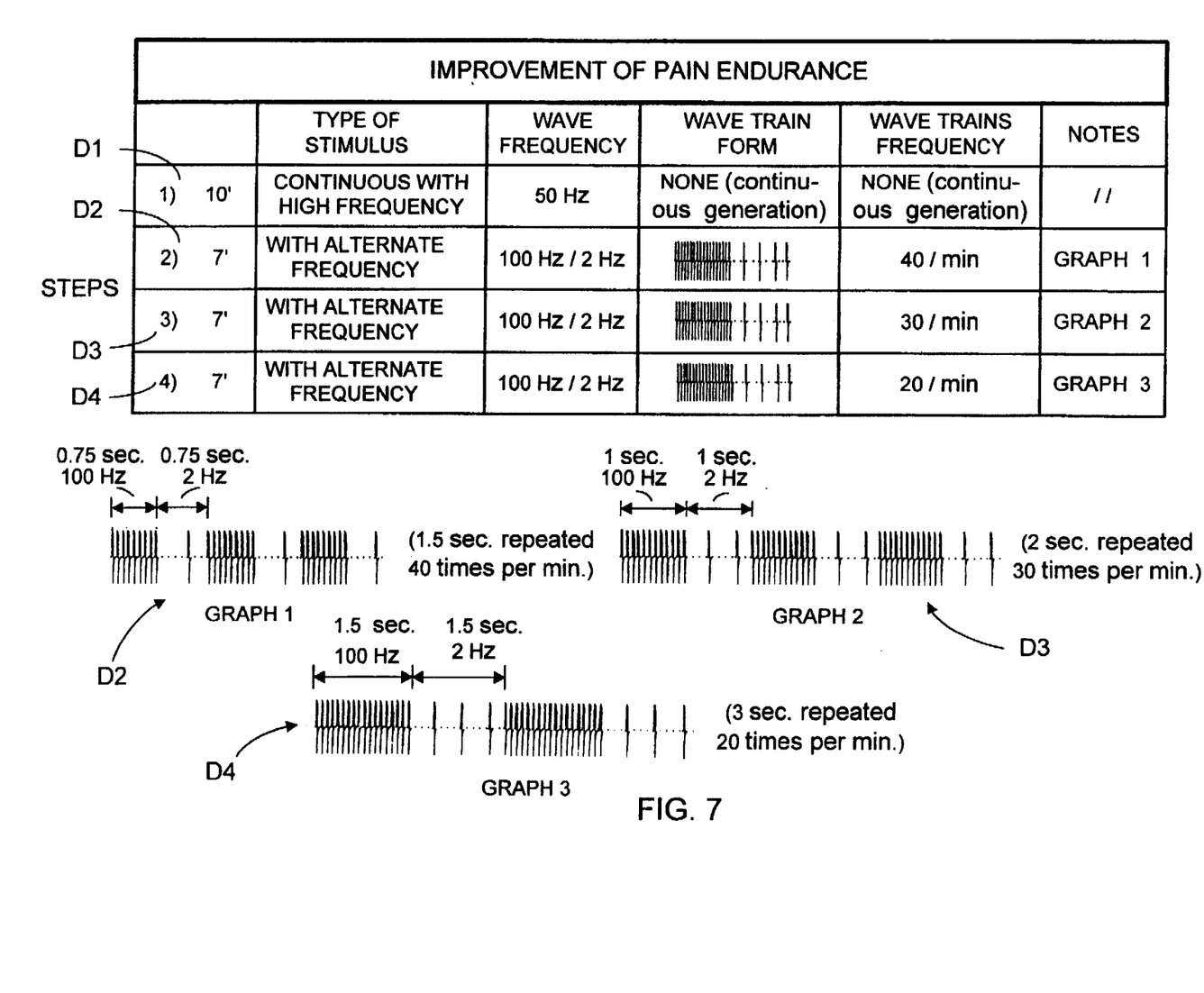

With reference to FIG. 7, the method of the invention is carried out by a sequence of steps, first D1, second D2, third D3 and fourth D4, which improve physical pain endurance of the human body.

The first step D1, lasting 10 minutes, employs the first wave train 1a with waves 10 of 50 hertz frequency.

The second step D2, lasting 7 minutes, employs the third wave train 1c, in which the period of each first bunch 4a and second bunch 4b is equal to 0.75 sec.

The third step D3 differs from the second step D2 only in that the period of each bunch 4a, 4b, is equal to 1 sec., while the fourth step D4 differs from the third one only because the period of each bunch 4a and 4b is equal to 1.50 sec.

Figure 8:
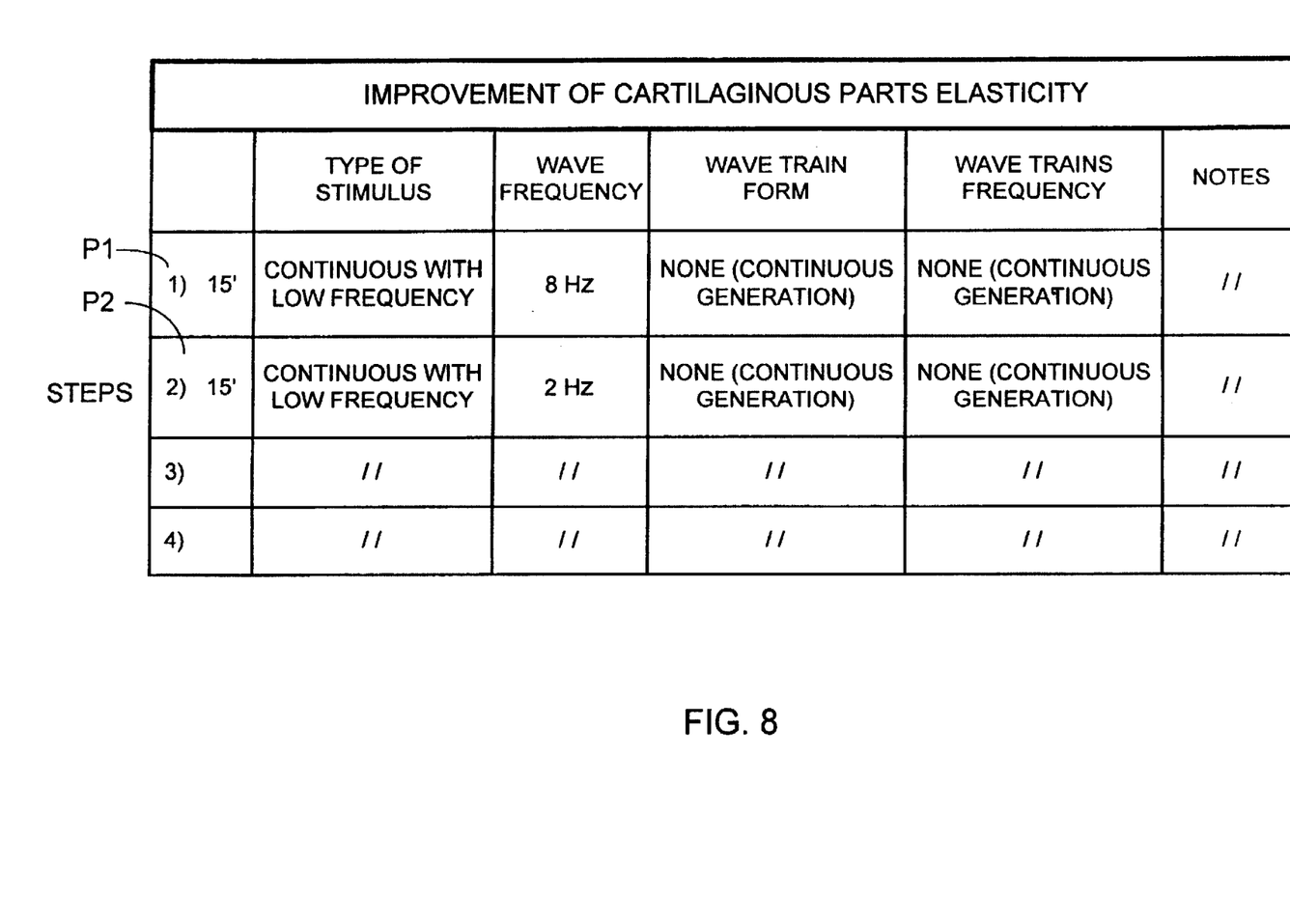

FIG. 8 illustrates a sequence of first step P1 and second step P2 that determine further development of the method and improve elasticity of cartilaginous parts of the human body, to which this sequence is applied.

The first step P1, lasting 15 minutes, employs continuously waves 10 of 8 hertz frequency, while in the second step P2, lasting 15 minutes, the waves 10 employed in the continuous way during the whole step, have 2 hertz frequency.

The main advantage of the present invention lies in the fact that the proposed method for improving certain functional characteristics of the human body can be employed in reasonably short time and moreover can be applied without help of specialized operators.

Another advantage of the present invention is that it proposes a method that can be applied to the human body in a simple way and that is extremely efficient in improving its functional characteristics.

It is understood that what above has been described as a pure example, non limitative, therefore all possible constructive variations remain within the scope of the present technical solution, as described above and claimed hereinafter.

What is claimed is:

1. A method of improving selected functional characteristics of a human body comprising, the steps of:

generating a wave train having a first bunch of waves of 100 hertz frequency, and a second bunch of waves of 2 hertz frequency, each said wave of each first and second bunch having a positive peak and a negative peak relative to a zero reference line and said second bunch having a period equal to the period of said first bunch;

grouping a plurality of said wave trains in a time-separated prefixed sequence; and applying said sequence of wave trains to a human body to generate a stimulus in the human body of alternating frequency.

2. A method as set forth in claim 1 which includes the steps of applying said sequence of wave trains for 10 minutes with said period of each bunch being 1 second;

thereafter applying said sequence of wave trains for 15 minutes with said period of each bunch being 1.50 seconds; and thereafter applying said sequence of wave trains for 15 minutes with said period of each bunch being 3 seconds, wherein the improved selected functional characteristic is for increasing blood circulation.

3. A method as set forth in claim 1 which includes the steps of applying said sequence of wave trains for 20 minutes with said period of each bunch being 1.25 seconds and each wave train having a constant positive peak and a constant negative peak;

thereafter applying said sequence of wave trains for 20 minutes with said period of each bunch being 1.875 seconds and each wave train having a constant positive peak and a constant negative peak;

thereafter applying a third sequence of wave trains for 10 minutes wherein each wave train of said third sequence of wave trains includes a single bunch of waves of 100 hertz frequency with a period of 3.5 seconds, each said single bunch of waves being of increasing amplitude over ⅔ of said period of said single bunch and of decreasing amplitude over a remaining ⅓ of said period of said single bunch to form an arrow-shaped wave train and wherein said arrow-shaped wave trains are separated over a 0.25 second time interval from each other, wherein the improved selected functional characteristic is for reduction of adipose substances.

4. A method as set forth in claim 1 which includes the steps of applying a continuous wave train of waves of 50 hertz frequency for 10 minutes;

thereafter applying said sequence of wave trains for 7 minutes with said period of each bunch being 0.75 seconds;

thereafter applying said sequence of wave trains for 7 minutes with said period of each bunch being 1 second; and thereafter applying said sequence of wave trains for 7 minutes with said period of each bunch being 1.50 seconds, wherein the improved selected functional characteristic is for improving pain endurance.

5. A method as set forth in claim 1 wherein each wave has a maximum peak of 80 volts.

6. A method as set forth in claim 1 wherein each positive peak has a width of 0.12 milliseconds.

* * * * *